US00PP34927P2

(12) United States Plant Patent
Koot

(10) Patent No.: US PP34,927 P2
(45) Date of Patent: Jan. 17, 2023

(54) ***VERBENA* PLANT NAMED 'DOVEREMFLACORE'**

(50) Latin Name: ***Verbena* X *hybrida***
Varietal Denomination: Doveremflacore

(71) Applicant: DUMMEN GROUP B.V., De Lier (NL)

(72) Inventor: Arjan Koot, Oeffelt (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 17/698,470

(22) Filed: Mar. 18, 2022

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
CPC ..... A01H 5/02; A01H 5/00; A01H 6/86
See application file for complete search history.

(56) References Cited

U.S. PATENT DOCUMENTS

PP25,771 P2 * 8/2015 Dummen ..... A01H 5/02
Plt./308

OTHER PUBLICATIONS

Dummen Orange Annuals 2021-2022, retrieved on Apr. 12, 2022 at https://online.flippingbook.com/view/398373771/, pp. 1,278-279. (Year: 2022).*

Germania Seed Company Lucas Greenhouses 2022 Plant Order Form, retrieved on Apr. 12, 2022 at https://germaniaseed.com/orderforms/2022/lucas_715_2022.pdf. pp. 1-3, 40. (Year: 2022).*

* cited by examiner

*Primary Examiner* — June Hwu
(74) *Attorney, Agent, or Firm* — C. Anne Whealy

(57) ABSTRACT

A new and distinct cultivar of *Verbena* plant named 'Doveremflacore', characterized by its mounding to semi-trailing plant habit; moderately vigorous growth habit and moderate growth rate; freely branching habit; early and freely flowering habit; large purplish red-colored flowers; and good container and garden performance.

1 Drawing Sheet

Botanical designation: *Verbena* X *hybrida*.
Cultivar denomination: 'DOVEREMFLACORE'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Verbena* plant, botanically known as *Verbena* X *hybrida* and hereinafter referred to by the name 'Doveremflacore'.

The new *Verbena* plant is a product of a planned breeding program conducted by the Inventor in Rheinberg, Germany. The objective of the breeding program is to create new freely branching and early flowering *Verbena* plants with numerous large and attractive flowers.

The new *Verbena* plant originated from a cross-pollination made by the Inventor in July, 2019 in Rheinberg, Germany of a proprietary selection of *Verbena* X *hybrida* identified as code number VV19-K0125, not patented, as the female, or seed, parent with a proprietary selection of *Verbena* X *hybrida* identified as code number VV19-K0203, not patented, as the male, or pollen, parent. The new *Verbena* plant was discovered and selected by the Inventor as a single flowering plant within the progeny of the stated cross-pollination in a controlled greenhouse environment in Rheinberg, Germany in May, 2021.

Asexual reproduction of the new *Verbena* plant by terminal vegetative cuttings in a controlled greenhouse environment in Rheinberg, Germany since June, 2021 has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dover emflacore'. These characteristics in combination distinguish 'Doveremflacore' as a new and distinct *Verbena* plant:

1. Mounding to semi-trailing plant habit.
2. Moderately vigorous growth habit and moderate growth rate.
3. Freely branching habit.
4. Early and freely flowering habit.
5. Large purplish red-colored flowers.
6. Good container and garden performance.

Plants of the new *Verbena* differ primarily from plants of the female parent selection in flower color as plants of the new *Verbena* have reddish-colored flowers than plants of the female parent selection.

Plants of the new *Verbena* differ primarily from plants of the male parent selection in flower color as plants of the new *Verbena* have darker-colored flowers than plants of the male parent selection.

Plants of the new *Verbena* can be compared to plants of the *Verbena hybrida* 'Duempflapich', disclosed in U.S. Plant Pat. No. 25,771. In side-by-side comparisons, plants of the new *Verbena* differ primarily from plants of 'Duempflapich' in the following characteristics:

1. Plants of the new *Verbena* have more flowers per inflorescence than plants of 'Duempflapich'.
2. Flowers of plants of the new *Verbena* are more reddish in color than flowers of plants of 'Duempflapich'.

BRIEF DESCRIPTION OF THE PHOTOGRAPH

The accompanying colored photograph illustrates the overall appearance of the new *Verbena* plant showing the colors as true as it is reasonably possible to obtain in colored reproductions of this type. Colors in the photograph may differ slightly from the color values cited in the detailed botanical description which accurately describe the colors of the new *Verbena* plant.

The photograph is a side perspective view of a typical flowering plant of 'Doveremflacore' grown in a container.

DETAILED BOTANICAL DESCRIPTION

The aforementioned photograph and following observations, measurements and values describe plants grown in 22-cm containers during the spring and early summer in a glass-covered greenhouse in Rheinberg, Germany and under cultural practices typical of commercial *Verbena* production. During the production of the plants, day and night temperatures averaged 18° C. and light levels averaged 4,500 lux. Plants were pinched one time three weeks after planting and were 25 weeks old when the photograph and description were taken. In the description, color references are made to The Royal Horticultural Society Colour Chart, Fifth Edition, except where general terms of ordinary dictionary significance are used.

Botanical classification: *Verbena* X *hybrida* 'Doveremflacore'.

Parentage:

*Female, or seed, parent*.—Proprietary selection of *Verbena* X *hybrida* identified as code number VV19-K0125, not patented.

*Male, or pollen, parent*.—Proprietary selection of *Verbena* X *hybrida* identified as code number VV19-K0203, not patented.

Propagation:

*Type*.—Terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; medium density.

Plant description:

*Plant habit*.—Mounding to semi-trailing plant habit; freely branching habit with about three primary lateral branches each with about twelve secondary lateral branches; pinching enhances lateral branch development; dense and bushy plant habit; moderately vigorous growth habit and moderate growth rate.

*Plant height, soil level to top of foliar plane*.—About 17 cm.

*Plant height, soil level to top of floral plane*.—About 24 cm.

*Plant diameter*.—About 75 cm.

Lateral branch description:

*Length*.—About 69 cm.

*Diameter*.—About 5.5 mm.

*Internode length*.—About 2.4 cm.

*Strength*.—Strong.

*Texture and luster*.—Pubescent; semi-glossy.

*Color, developing*.—Close to 145A and at the internodes, close to 145B.

*Color, developed*.—Close to 146A.

Leaf description:

*Arrangement*.—Opposite, simple.

*Length*.—About 4.2 cm.

*Width*.—About 2.3 cm.

*Shape*.—Lanceolate.

*Apex*.—Acute.

*Base*.—Attenuate.

*Margin*.—Lobed; sinuses medium in depth and divergent.

*Texture and luster, upper surface*.—Pubescent, coarse; semi-glossy.

*Texture and luster, lower surface*.—Pubescent, coarse; matte.

*Venation pattern*.—Pinnate.

*Color*.—Developing leaves, upper surface: Close to N137C. Developing leaves, lower surface: Close to 138B. Fully expanded leaves, upper surface: Close to 137A; venation, close to 144C. Fully expanded leaves, lower surface: Close to 138B; venation, close to 145C.

*Petioles*.—Length: About 4.5 mm. Diameter: About 2 mm. Strength: Moderately strong. Texture and luster, upper and lower surfaces: Smooth, glabrous; matte. Color, upper surface: Close to 145C. Color, lower surface: Close to 145B.

Flower description:

*Flower arrangement and habit*.—Salverform flowers arranged in hemispherical terminal umbels; umbels dense and mounding; numerous umbels per plant; flowers face upward or outwardly depending on position in the umbel; freely flowering habit with about 26 flowers per inflorescence and about 325 flowers and flower buds per plant at one time.

*Fragrance*.—None detected.

*Natural flowering season*.—Plants flower continuously from the spring through the fall in Germany; plants begin flowering about eight weeks after planting.

*Flower longevity*.—Individual flowers last about one week on the plant; flowers persistent.

*Inflorescence height*.—About 2.7 cm.

*Inflorescence diameter*.—About 5.5 cm.

*Flower buds*.—Length: About 1.6 cm. Diameter: About 2.7 mm. Shape: Oval to tubular. Texture and luster: Rippled; matte. Color: Close to 63A.

*Flowers*.—Appearance: Salverform, five-parted fused corolla. Diameter: About 2.5 cm. Depth: About 3.1 cm. Throat diameter: About 2 mm. Tube length: About 2.1 cm. Tube diameter: About 2.4 mm.

*Corolla*.—Arrangement: Single whorl of five fused petals. Petal lobe length: About 1.2 cm. Petal lobe width: About 1.3 cm. Petal lobe shape: Obovate, flat. Petal lobe apex: Emarginate. Petal margin: Entire. Petal texture and luster, upper and lower surfaces: Smooth, glabrous; matte. Throat texture and luster: Smooth, glabrous; matte. Tube texture and luster: Smooth, glabrous; matte. Color: Petal lobe, when opening, upper surface: Close to 52A. Petal lobe, when opening, lower surface: Close to 58C. Petal lobe, fully opened, upper surface: Close to 58B; venation, close to 58B; color does not change with subsequent development. Petal lobe, fully opened, lower surface: Close to N57D; venation, close to N57D; color does not change with subsequent development. Throat: Close to 145A; venation, close to 145A. Tube: Close to 145D; venation, close to 145D.

*Calyx*.—Arrangement: Star-shaped calyx with five fused sepals. Length: About 1.3 cm. Diameter: About 3 mm. Sepal length: About 1.3 cm. Sepal width: About 1 mm. Sepal shape: Ligulate. Sepal apex: Acute. Sepal margin: Entire. Sepal texture and luster, upper surface: Pubescent, coarse; semi-glossy. Sepal texture and luster, lower surface: Pubescent, coarse; matte. Sepal color, when developing, upper and lower surfaces: Close to 145C and 143A. Sepal color, fully developed, upper and lower surfaces: Close to 145C and 143A.

*Peduncles*.—Length: About 3.8 cm. Diameter: About 1.3 mm. Strength: Strong. Aspect: Mostly upright. Texture and luster: Pubescent; semi-glossy. Color: Close to 144B.

*Pedicels*.—Length: About 0.5 mm. Diameter: About 0.5 mm. Strength: Strong. Aspect: Mostly upright. Texture and luster: Smooth, glabrous; semi-glossy. Color: Close to 144A.

*Reproductive organs*.—Stamens: Quantity and arrangement: About four per flower, adnate to corolla tube. Filament length: About 0.5 mm. Filament color: Close to 145C. Anther length: About 0.8 mm. Anther shape: Oval. Anther color: Close to N144D. Pollen amount: Moderate. Pollen color: Close to 2B. Pistils: Quantity: One per flower. Pistil length: About 1.9 cm. Style length: About 1.8 cm. Style color: Close to 144D. Stigma diameter: About 1 mm. Stigma shape: Bi-parted; fimbriate. Stigma color: Close to 144B. Ovary color: Close to N144D. Fruits: Quantity produced per plant: About 470 during the flowering season. Length: About 5 mm. Diameter: About 1 mm. Texture: Rough. Color: Close to 199C. Seeds: Quantity per flower: About four. Length: About 4.8 mm. Diameter: About 0.8 mm. Texture: Smooth, glabrous. Color: Close to 199B.

Garden performance: Plants of the new *Verbena* have been observed to have good garden performance, to tolerate temperatures ranging from 5° C. to 40° C. and to be suitable for USDA Hardiness Zone 11.

Pathogen & pest resistance: To date, plants of the new *Verbena* have not been observed to be resistant to pathogens and pests common to *Verbena* plants.

It is claimed:

1. A new and distinct *Verbena* plant named 'Doveremflacore' as illustrated and described.

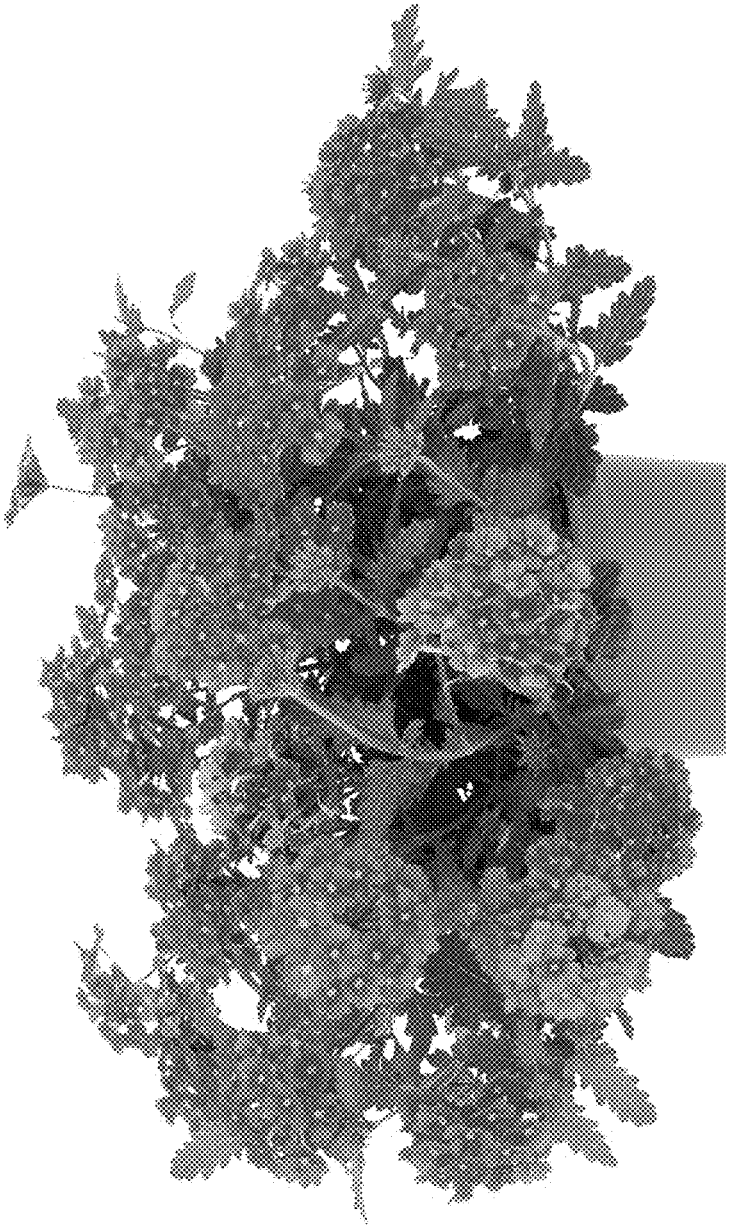

* * * * *